US 11,051,800 B2

(12) United States Patent
Mitelberg et al.

(10) Patent No.: US 11,051,800 B2
(45) Date of Patent: Jul. 6, 2021

(54) ENDOSCOPIC SUTURING SYSTEM HAVING EXTERNAL INSTRUMENT CHANNEL

(71) Applicant: Apollo Endosurgery, Inc., Austin, TX (US)

(72) Inventors: Vladimir Mitelberg, Austin, TX (US); Thomas Neudeck, Austin, TX (US); John Mims, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 955 days.

(21) Appl. No.: 15/233,737

(22) Filed: Aug. 10, 2016

(65) Prior Publication Data

US 2018/0042602 A1     Feb. 15, 2018

(51) Int. Cl.
*A61B 17/04*        (2006.01)
*A61B 1/018*        (2006.01)
(Continued)

(52) U.S. Cl.
CPC ........ *A61B 17/0469* (2013.01); *A61B 1/0014* (2013.01); *A61B 1/00087* (2013.01);
(Continued)

(58) Field of Classification Search
CPC ............ A61B 17/0469; A61B 1/00101; A61B 1/00087; A61B 1/0014; A61B 1/018; A61B 2017/306; A61B 2017/06042; A61B 2017/00314; A61B 2017/00296; A61B 2017/00349
See application file for complete search history.

(56) References Cited

U.S. PATENT DOCUMENTS

| | | |
|---|---|---|
| 3,001,522 A | 9/1961 | Silverman |
| 3,495,703 A | 2/1970 | Calabrese |

(Continued)

FOREIGN PATENT DOCUMENTS

| | | |
|---|---|---|
| WO | WO 2008/069816 | 6/2008 |
| WO | WO2015052320 A1 | 4/2015 |

OTHER PUBLICATIONS

U.S. Appl. No. 61/483,679, filed May 8, 2011, Vladimir Mitelberg.
(Continued)

*Primary Examiner* — Tan-Uyen T Ho
*Assistant Examiner* — Rachel S Highland
(74) *Attorney, Agent, or Firm* — Brian Szymczak

(57) ABSTRACT

An endoscopic suturing system includes an endoscope, a suturing device, a needle assembly movable through tissue by the suturing device, and first and second devices used in association with the suturing device. The cap assembly includes a rotatable needle arm supporting the needle assembly and actuatable by a proximal handle via a transmission assembly. First and second separate lumen extends outside the endoscope from the cap assembly to a proximal handle to advance instruments therethrough to engage the needle assembly and target the tissue. The cap assembly is retained at an end of the endoscope by a securing arm. The securing arm may be resilient or rotatable. Ancillary clips are also provided about the first and second lumen and transmission assembly to couple them to the endoscope.

27 Claims, 8 Drawing Sheets

(51) Int. Cl.
*A61B 1/00* (2006.01)
*A61B 17/062* (2006.01)
*A61B 17/00* (2006.01)
*A61B 17/30* (2006.01)
*A61B 17/06* (2006.01)

(52) U.S. Cl.
CPC .......... *A61B 1/00101* (2013.01); *A61B 1/018* (2013.01); *A61B 17/0625* (2013.01); *A61B 2017/00296* (2013.01); *A61B 2017/00314* (2013.01); *A61B 2017/00349* (2013.01); *A61B 2017/06042* (2013.01); *A61B 2017/306* (2013.01)

(56) References Cited

U.S. PATENT DOCUMENTS

| | | |
|---|---|---|
| 3,603,492 A | 9/1971 | Schantz |
| 3,749,328 A | 7/1973 | Dusenbery |
| 3,901,244 A | 8/1975 | Schweizer |
| 4,084,692 A | 4/1978 | Bilweis |
| 4,183,431 A | 1/1980 | Schmidt et al. |
| D263,505 S | 3/1982 | Black |
| 4,794,911 A | 1/1989 | Okada |
| 5,026,379 A | 6/1991 | Yoon |
| 5,041,129 A | 8/1991 | Hayhurst et al. |
| 5,131,534 A | 7/1992 | Brown et al. |
| 5,141,520 A | 8/1992 | Goble et al. |
| 5,196,022 A | 3/1993 | Bilweis |
| 5,217,486 A | 6/1993 | Rice et al. |
| 5,249,671 A | 10/1993 | Sinn |
| 5,263,585 A | 11/1993 | Lawhon et al. |
| 5,284,240 A | 2/1994 | Alpern et al. |
| 5,304,185 A | 4/1994 | Taylor |
| 5,307,924 A | 5/1994 | Manosalva et al. |
| 5,356,424 A | 10/1994 | Buzerak et al. |
| 5,364,408 A | 11/1994 | Gordon |
| 5,403,328 A | 4/1995 | Shallman |
| 5,407,071 A | 4/1995 | Lawhon et al. |
| 5,433,725 A | 7/1995 | Christian et al. |
| 5,437,266 A | 8/1995 | McPherson et al. |
| 5,454,823 A | 10/1995 | Richardson et al. |
| 5,464,424 A | 11/1995 | O'Donnell, Jr. |
| 5,466,241 A | 11/1995 | Leroy et al. |
| 5,470,338 A | 11/1995 | Whitfield et al. |
| 5,474,568 A | 12/1995 | Scott |
| 5,478,344 A | 12/1995 | Stone et al. |
| 5,478,345 A | 12/1995 | Stone et al. |
| 5,514,159 A | 5/1996 | Matula et al. |
| 5,520,702 A | 5/1996 | Sauer et al. |
| 5,527,321 A | 6/1996 | Hinchliffe |
| 5,545,180 A | 8/1996 | Le et al. |
| 5,573,496 A | 11/1996 | McPherson et al. |
| 5,575,800 A | 11/1996 | Gordon |
| 5,584,860 A | 12/1996 | Goble et al. |
| 5,584,861 A | 12/1996 | Swan et al. |
| 5,601,557 A | 2/1997 | Hayhurst |
| 5,626,590 A | 5/1997 | Wilk |
| 5,626,614 A | 5/1997 | Hart |
| 5,628,395 A | 5/1997 | Daniele et al. |
| 5,643,320 A | 7/1997 | Lower et al. |
| 5,649,940 A | 7/1997 | Hart et al. |
| 5,653,717 A | 8/1997 | Ko et al. |
| 5,662,588 A | 9/1997 | Iida |
| 5,662,658 A | 9/1997 | Wenstrom, Jr. |
| 5,669,917 A | 9/1997 | Sauer et al. |
| 5,681,331 A | 10/1997 | De La Torre et al. |
| 5,685,823 A | 11/1997 | Ito et al. |
| 5,690,655 A | 11/1997 | Hart et al. |
| 5,700,272 A | 12/1997 | Gordon et al. |
| 5,707,379 A | 1/1998 | Fleenor et al. |
| 5,713,910 A | 2/1998 | Gordon et al. |
| 5,720,766 A | 2/1998 | Zang et al. |
| 5,733,293 A | 3/1998 | Scirica et al. |
| 5,741,277 A | 4/1998 | Gordon |
| 5,755,729 A | 5/1998 | De la Torre et al. |
| 5,765,740 A | 6/1998 | Ferguson |
| 5,782,862 A | 7/1998 | Bonutti |
| 5,792,152 A | 8/1998 | Klein et al. |
| 5,792,153 A | 8/1998 | Swain et al. |
| 5,810,848 A | 9/1998 | Hayhurst |
| 5,814,054 A | 9/1998 | Kortenbach et al. |
| 5,814,071 A | 9/1998 | McDevitt et al. |
| 5,817,013 A | 10/1998 | Ginn et al. |
| 5,819,918 A | 10/1998 | Scanlon |
| 5,824,009 A | 10/1998 | Fukuda et al. |
| 5,833,055 A | 11/1998 | Cerwin et al. |
| 5,843,099 A | 12/1998 | Nichols et al. |
| 5,860,992 A | 1/1999 | Daniel et al. |
| 5,879,371 A | 3/1999 | Gardiner et al. |
| 5,887,594 A | 3/1999 | LoCicero, III |
| 5,891,160 A | 4/1999 | Williamson, IV et al. |
| 5,897,563 A | 4/1999 | Yoon et al. |
| 5,897,564 A | 4/1999 | Schulze et al. |
| 5,910,105 A | 6/1999 | Swain et al. |
| 5,918,733 A | 7/1999 | Cerwin et al. |
| 5,944,739 A | 8/1999 | Zlock et al. |
| 5,947,982 A | 9/1999 | Duran |
| 5,951,587 A | 9/1999 | Quereshi et al. |
| 5,954,731 A | 9/1999 | Yoon |
| 5,954,732 A | 9/1999 | Hart et al. |
| 5,954,733 A | 9/1999 | Yoon |
| 5,964,764 A | 10/1999 | West, Jr. et al. |
| 5,993,466 A | 11/1999 | Yoon |
| 5,993,467 A | 11/1999 | Yoon |
| 6,010,525 A | 1/2000 | Bonutti et al. |
| 6,036,699 A | 3/2000 | Andreas et al. |
| 6,048,351 A | 4/2000 | Gordon et al. |
| 6,053,935 A | 4/2000 | Brenneman et al. |
| 6,068,648 A | 5/2000 | Cole et al. |
| 6,071,233 A | 6/2000 | Ishikawa et al. |
| 6,071,289 A | 6/2000 | Stefanchik et al. |
| 6,077,286 A | 6/2000 | Cuschieri et al. |
| 6,086,600 A | 7/2000 | Kortenbach |
| 6,086,601 A | 7/2000 | Yoon |
| 6,086,608 A | 7/2000 | Ek et al. |
| 6,095,323 A | 8/2000 | Ferguson |
| 6,096,051 A | 8/2000 | Kortenbach et al. |
| 6,117,144 A | 9/2000 | Nobles et al. |
| 6,126,666 A | 10/2000 | Trapp et al. |
| 6,135,385 A | 10/2000 | Martinez de Lahidalga |
| 6,136,010 A | 10/2000 | Modesitt et al. |
| RE36,974 E | 11/2000 | Bonutti |
| 6,149,658 A | 11/2000 | Gardiner et al. |
| 6,159,234 A | 12/2000 | Bonutti et al. |
| 6,171,316 B1 | 1/2001 | Kovac et al. |
| 6,224,614 B1 | 5/2001 | Yoon |
| 6,277,064 B1 | 8/2001 | Yoon |
| 6,277,132 B1 | 8/2001 | Brhel |
| 6,293,961 B2 | 9/2001 | Schwartz et al. |
| 6,306,081 B1 | 10/2001 | Ishikawa |
| 6,312,448 B1 | 11/2001 | Bonutti |
| 6,352,503 B1 | 3/2002 | Matsui et al. |
| 6,358,259 B1 | 3/2002 | Swain et al. |
| 6,443,962 B1 | 9/2002 | Gaber |
| 6,467,612 B1 | 10/2002 | Rosenfeld |
| 6,475,230 B1 | 11/2002 | Bonutti et al. |
| 6,533,795 B1 | 3/2003 | Tran et al. |
| 6,533,796 B1 | 3/2003 | Sauer et al. |
| 6,569,085 B2 | 5/2003 | Kortenbach et al. |
| 6,585,744 B1 | 7/2003 | Griffith |
| 6,596,001 B2 | 7/2003 | Stormby et al. |
| 6,635,073 B2 | 10/2003 | Bonutti |
| 6,656,182 B1 | 12/2003 | Hayhurst |
| 6,663,639 B1 | 12/2003 | Laufer et al. |
| 6,663,641 B1 | 12/2003 | Kovac et al. |
| 6,663,643 B2 | 12/2003 | Field et al. |
| 6,695,852 B2 | 2/2004 | Gleason |
| 6,699,183 B1 | 3/2004 | Wimmer |
| 6,719,763 B2 | 4/2004 | Chung et al. |
| 6,719,764 B1 | 4/2004 | Gellman et al. |
| 6,733,509 B2 | 5/2004 | Nobles et al. |
| 6,740,030 B2 | 5/2004 | Martone et al. |
| 6,755,843 B2 | 6/2004 | Chung et al. |

(56) References Cited

U.S. PATENT DOCUMENTS

| | | |
|---|---|---|
| 6,804,937 B2 | 10/2004 | Dey et al. |
| 6,808,491 B2 | 10/2004 | Kortenbach et al. |
| 6,866,673 B2 | 3/2005 | Oren et al. |
| 6,893,393 B2 | 5/2005 | Carillo |
| 6,896,686 B2 | 5/2005 | Weber |
| 6,921,361 B2 | 7/2005 | Suzuki et al. |
| 6,921,408 B2 | 7/2005 | Sauer |
| 6,923,819 B2 | 8/2005 | Meade et al. |
| 6,955,643 B2 | 10/2005 | Gellman et al. |
| 6,966,916 B2 | 11/2005 | Kumar |
| 6,988,985 B2 | 1/2006 | Suzuki et al. |
| 6,988,987 B2 | 1/2006 | Ishikawa et al. |
| 6,997,931 B2 | 2/2006 | Sauer et al. |
| 7,033,370 B2 | 4/2006 | Gordon et al. |
| 7,033,379 B2 | 4/2006 | Peterson |
| 7,041,111 B2 | 5/2006 | Chu |
| 7,048,755 B2 | 5/2006 | Bonutti et al. |
| 7,060,025 B2 | 6/2006 | Long et al. |
| 7,060,077 B2 | 6/2006 | Gordon et al. |
| 7,063,710 B2 | 6/2006 | Takamoto et al. |
| 6,986,737 B2 | 7/2006 | Suzuki et al. |
| 7,070,044 B2 | 7/2006 | Rosenfeld |
| 7,083,630 B2 | 8/2006 | DeVries et al. |
| 7,083,638 B2 | 8/2006 | Foerster |
| 7,087,012 B2 | 8/2006 | Ishibiki |
| 7,090,686 B2 | 8/2006 | Nobles et al. |
| 7,090,690 B2 | 8/2006 | Foerster et al. |
| 7,094,246 B2 | 8/2006 | Anderson et al. |
| 7,112,208 B2 | 9/2006 | Morris |
| 7,131,979 B2 | 11/2006 | DiCarlo et al. |
| 7,144,401 B2 | 12/2006 | Yamamoto et al. |
| 7,147,652 B2 | 12/2006 | Bonutti et al. |
| 7,150,757 B2 | 12/2006 | Fallin et al. |
| 7,153,314 B2 | 12/2006 | Laufer et al. |
| 7,175,636 B2 | 2/2007 | Yamamoto et al. |
| 7,179,277 B2 | 2/2007 | Cunningham |
| 7,191,900 B2 | 3/2007 | Opie et al. |
| 7,198,599 B2 | 4/2007 | Goto et al. |
| 7,204,802 B2 | 4/2007 | De Leval |
| 7,220,266 B2 | 5/2007 | Gambale |
| 7,223,230 B2 | 5/2007 | Zirps et al. |
| 7,235,086 B2 | 6/2007 | Sauer et al. |
| 7,264,624 B2 | 9/2007 | Nash et al. |
| 7,318,802 B2 | 1/2008 | Suzuki et al. |
| 7,322,161 B2 | 1/2008 | Prescott |
| 7,326,221 B2 | 2/2008 | Sakamoto et al. |
| 7,338,504 B2 | 3/2008 | Gibbens, III et al. |
| 7,344,545 B2 | 3/2008 | Takemoto et al. |
| 7,371,215 B2 | 5/2008 | Colliou et al. |
| 7,431,694 B2 | 10/2008 | Stefanchik et al. |
| 7,445,603 B2 | 11/2008 | Zimmon |
| 7,527,590 B2 | 5/2009 | Suzuki et al. |
| 7,566,300 B2 | 7/2009 | Devierre et al. |
| 7,575,548 B2 | 8/2009 | Takemoto et al. |
| 7,601,161 B1 | 10/2009 | Nobles et al. |
| 7,637,369 B2 | 12/2009 | Kennedy et al. |
| 7,665,279 B2 | 2/2010 | Prescott |
| 7,703,459 B2 | 4/2010 | Saadat et al. |
| 7,727,144 B2 | 6/2010 | Suzuki |
| 7,766,162 B2 | 8/2010 | Maki et al. |
| 7,775,973 B2 | 8/2010 | Okada et al. |
| 7,776,066 B2 | 8/2010 | Onuki et al. |
| 7,785,348 B2 | 8/2010 | Kuhns et al. |
| 7,918,867 B2 | 4/2011 | Dana et al. |
| 7,931,661 B2 | 4/2011 | Saadat et al. |
| 7,935,128 B2 | 5/2011 | Rioux et al. |
| 7,988,656 B2 | 8/2011 | Uesugi et al. |
| 8,016,840 B2 | 9/2011 | Takemoto et al. |
| 8,021,376 B2 | 9/2011 | Takemoto et al. |
| 8,287,556 B2 | 10/2012 | Gilkey et al. |
| 8,679,136 B2 | 3/2014 | Mitelberg |
| 9,198,562 B2 | 12/2015 | Mitelberg et al. |
| 2002/0040227 A1 | 4/2002 | Harari et al. |
| 2002/0087190 A1 | 7/2002 | Benavitz et al. |
| 2003/0176762 A1 | 9/2003 | Kammerer |
| 2003/0176880 A1 | 9/2003 | Long et al. |
| 2003/0181924 A1 | 9/2003 | Yamamoto et al. |
| 2004/0015177 A1 | 1/2004 | Chu |
| 2004/0249393 A1 | 12/2004 | Weisel et al. |
| 2005/0065401 A1 | 3/2005 | Saadat et al. |
| 2005/0149067 A1 | 7/2005 | Takemoto et al. |
| 2005/0234297 A1* | 10/2005 | Devierre ............ A61B 1/00087 600/153 |
| 2005/0250984 A1 | 11/2005 | Lam et al. |
| 2005/0250985 A1 | 11/2005 | Saadat et al. |
| 2006/0258906 A1* | 11/2006 | Binmoeller ........ A61B 1/00135 600/114 |
| 2006/0281970 A1 | 12/2006 | Stokes et al. |
| 2008/0039255 A1 | 2/2008 | Jinno et al. |
| 2008/0045979 A1 | 2/2008 | Ma |
| 2009/0187069 A1* | 7/2009 | Terliuc ............... A61B 1/00142 600/106 |
| 2009/0236399 A1* | 9/2009 | Bilotti .................. A61B 17/072 227/180.1 |
| 2009/0312775 A1 | 12/2009 | Gilkey et al. |
| 2010/0036198 A1 | 2/2010 | Tacchino et al. |
| 2010/0298630 A1 | 11/2010 | Wingall |
| 2011/0099773 A1 | 5/2011 | Golden et al. |
| 2012/0016191 A1* | 1/2012 | Ito ...................... A61B 1/00087 600/104 |
| 2012/0150200 A1* | 6/2012 | Mitelberg .......... A61B 1/00087 606/147 |
| 2012/0271327 A1 | 10/2012 | West et al. |
| 2013/0006287 A1 | 1/2013 | West et al. |
| 2016/0045197 A1 | 2/2016 | Mitelberg et al. |

OTHER PUBLICATIONS

U.S. Appl. No. 61/495,970, filed Jun. 11, 2011, Vladimir Mitelberg.
U.S. Appl. No. 61/073,340, filed Jun. 17, 2008, J. Landon Gilkey.
U.S. Appl. No. 61/162,249, filed Mar. 20, 2009, J. Landon Gilkey.

* cited by examiner

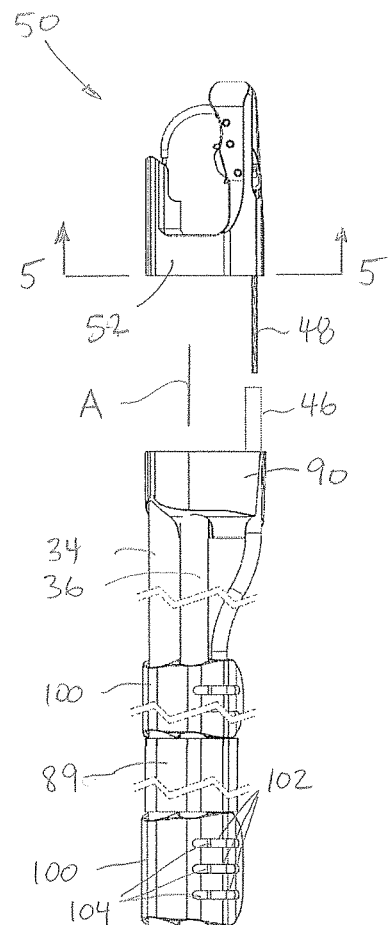
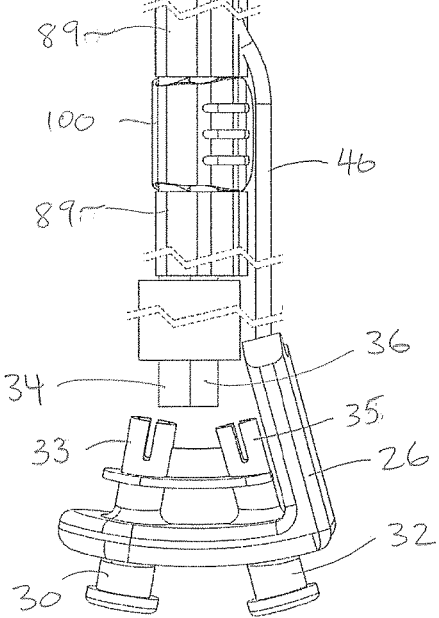
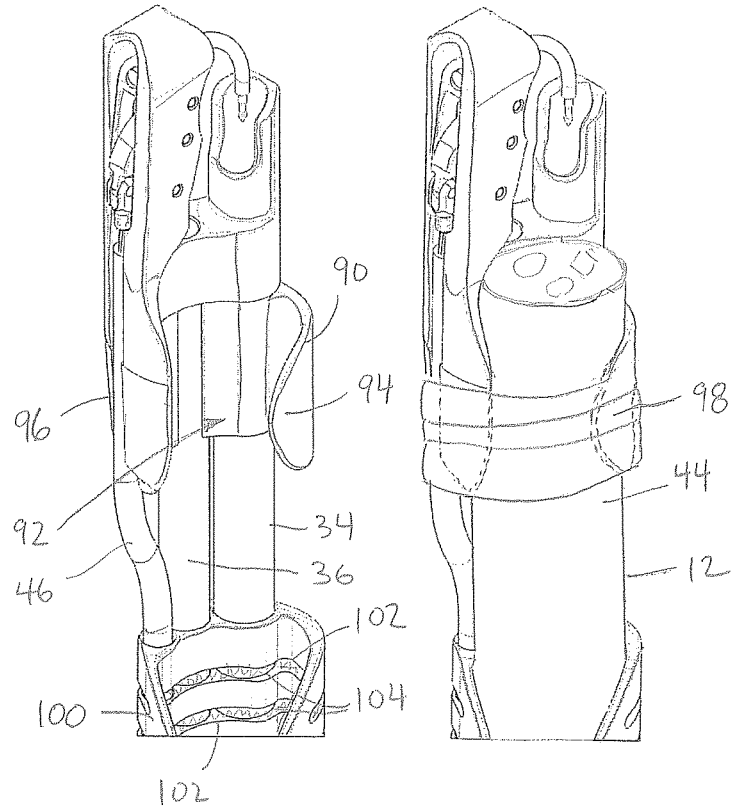
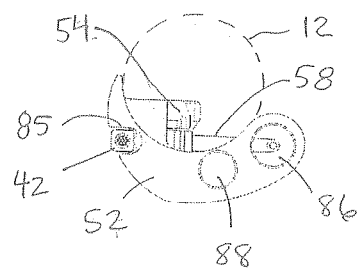
FIG. 3
FIG. 6
FIG. 7
FIG. 5

ENDOSCOPIC SUTURING SYSTEM HAVING EXTERNAL INSTRUMENT CHANNEL

CROSS-REFERENCE TO RELATED APPLICATIONS

This application is related to U.S. Pat. Nos. 8,287,556, 8,679,136, and 9,198,562, which are hereby incorporated by reference herein in their entireties.

This application is also related to U.S. Ser. No. 13/327,988, filed Dec. 16, 2011, Ser. No. 13/539,661, filed Jul. 2, 2012, and Ser. No. 13/539,777, filed Jul. 2, 2012, all of which are hereby incorporated by reference herein in their entireties.

BACKGROUND OF THE INVENTION

1. Field of the Invention

The present invention relates to a treatment device which can be inserted into a body through a natural orifice with an endoscope or other steerable guide member. The present invention may be used to perform suturing on the tissue of a mammal, whether human or not, and whether or not alive, but is not limited thereto.

2. State of the Art

U.S. Pat. No. 7,344,545 to Takemoto discloses an endoscopic suturing system having many embodiments to perform a surgical operation. This suturing system generally comprises an assembly having first and second arms which are actuatable by a push rod to rotatably approach each other while one arm grasps tissue and the second arm drives a curved needle through the tissue. The system also includes a needle recovery member requiring a rigid alignment with the curved needle arm. While this system affords the ability to grasp thick tissue, the tissue grasping arm and the arrangement of the needle recovery member provides bulk to the system making it difficult to use in endoscopic procedures.

Co-owned U.S. Pat. No. 8,287,556 to Gilkey et al. describes a system that addresses various limitations of the system by Takemoto. Gilkey describes an endoscopic treatment device having a structure enabling a small profile for delivery while providing an end effector with both a wide opening and closing angle that produces the large needle force for piercing tissue to perform a surgical operation such as tissue approximation and suturing within the body.

The Gilkey system comprises a transmission assembly coupled to a proximal handle assembly for operation outside of the body and a distal cap assembly where the cap assembly is adapted to engage the distal end of an endoscope. The transmission assembly is connected to a link mechanism and is actuated to cause a needle assembly having a needle holder arm and needle coupled to the cap assembly to move in a direction to puncture tissue and a direction to be removed from tissue. The endoscope to which the cap assembly is coupled has first and second instrument channels to receive cooperative devices therethrough. The first device is positioned within the first instrument channel of the endoscope and has a distal end adapted to receive and grasp the needle and a proximal end coupled to a handle assembly. The second device is positioned within the second instrument channel of the endoscope to engage tissue, and draw the tissue back into the path of the needle so that the tissue can be pierced by the needle as the needle is moved from an open to a closed position.

While the Gilkey system works very well, it presently requires association with an endoscope having two instrument channels. This may limit use of the system to larger endoscopes with such features. However, smaller endoscopes are gaining favor. Such smaller endoscopes, with their smaller profile, can be more easily advanced through a natural orifice. However, the reduced profile of the smaller endoscopes cannot accommodate the two instrument channels required for the Gilkey suturing system.

SUMMARY OF THE INVENTION

An endoscopic suturing system includes an endoscope, a suturing device, a needle assembly movable through tissue by the suturing device, and first and second devices used in association with the suturing device.

In accord with an embodiment, the endoscope can be a small profile endoscope, generally 5-10 mm in diameter, and can have one or more instrument channels, and optionally no instrument channel. As such, the number of instrument channels is not critical to operation of the system. The endoscope includes a distal end and a proximal end.

The suturing device includes a distal cap assembly adapted to be mounted at the distal end of the endoscope, and transmission assembly extending between the cap assembly and a proximal handle adapted to apply a force to the transmission assembly and operate the cap assembly remotely from the distal cap assembly. The cap assembly includes a mount, a support bracket extending distally from the mount, and a needle arm rotatably mounted on the bracket. A bell crank is also rotatably mounted on the support bracket and engages the needle arm. The distal end of the transmission assembly is attached to the bell crank, such that when the transmission assembly is operated by the handle, movement of the bell crank causes rotation of the needle arm between the open and closed positions. The needle assembly includes a needle body, a needle tip with a tissue-piercing end, and suture coupled to the needle body. The needle arm couples to the needle assembly at the needle body.

In accord with one aspect of the embodiment, the mount of the cap assembly also includes a first throughbore and a second throughbore. The first throughbore is positioned in alignment with the needle arm and needle when the needle arm is in the closed position. A needle guide extends distally from over the first throughbore. The second throughbore is positioned between the first throughbore and the support bracket. The mount is structured such that when the cap assembly is coupled to the endoscope, the first and second throughbores are positioned radially outside the profile of the endoscope. In accord with another aspect of the embodiment, the cap is coupled to the distal end of the endoscope with a peripheral engagement structure in the form of a resilient cap clip integrated with the mount.

First and second lumen, each including a distal end and a proximal end, extend from the first and second throughbores, respectively, external of the endoscope, to the proximal handle. The distal end of the first lumen is fixed in the first throughbore, and its proximal end is coupled to a first connector on the handle. The distal end of the second lumen is fixed in the second throughbore, and its proximal end is coupled a second connector on the handle. The first and second lumen may be defined by discrete catheters or integrated into a common catheter. The catheters or catheter may be covered in a common sheath.

The first lumen is adapted to receive a first device that has a distal end effector that can receive and grasp the needle. The second lumen is adapted to receive a second device that has a distal end effector that can engage tissue, and draw the tissue back into the path of the needle so that the tissue can be pierced by the needle as the needle is moved from an open to a closed position.

A plurality of ancillary clips are provided about the first and second lumen and transmission assembly to couple them to the endoscope. The ancillary clips are longitudinally spaced apart along the lumens and transmission assembly to allow suitable flexure and operation of the first and second devices extending within the first and second lumen, as well as operation of the transmission assembly.

The proximal handle includes a lever operated handle coupled to the transmission assembly for operating the transmission assembly, a bracket including first and second ports communicating with the respective first and second connectors coupled to the first and second lumen, and a collar that attaches the handle to the endoscope.

In accord with another embodiment, substantially similar to the suturing system described above, the cap includes a peripheral engagement structure in the form of a rotatable arm integrated with the mount that captures the endoscope.

In use, the suturing device is coupled to an endoscope and prepared for use. In so coupling, the cap assembly is attached to the distal end of the endoscope, with the cap clip or rotatable arm being opened to laterally receive the endoscope, and then closed to secure the cap assembly and endoscope relative to each other. The first and second lumen and transmission assembly are coupled along the endoscope with the supplemental clips. The collar is properly positioned at the handle of the endoscope. The first device is advanced through the first port, into the first lumen and to the cap assembly. A needle assembly is loaded onto the needle arm.

The distal end of the endoscope and cap assembly of the suturing device are advanced into a natural orifice of a patient, optionally through a guide tube, and approached to target tissue. The handle of the suturing device is operated to move the needle arm into the open position. The end effector of the second device is advanced through the second port, into the second lumen, and beyond the cap assembly. The end effector of the second device is operated to engage tissue and the second device is retracted to draw the tissue in a fold into the path of the needle. The handle is then operated to move the needle arm into the closed position, piercing the tissue fold and passing the suture through the tissue fold during the movement. As the needle enters the closed position, it is securely engaged by the end effector of the first device. The handle is then operated to move the needle arm toward the open position, thereby disengaging the needle arm from the needle. The end effector of the second device is released from the tissue. The endoscope is then moved or operated to displace the cap assembly relative to the sutured tissue fold. The needle and suture may be secured onto the tissue, such as by knotting or cinching, or the needle may be repositioned in engagement with the needle arm and additional suture loops may be formed within adjacent or other areas of tissue. Once the suturing is complete, the needle arm is returned to a closed position, and the endoscope and suturing device are removed from the patient.

The suturing assembly is then released from over the endoscope by releasing the peripheral engagement structure and ancillary clips from over the endoscope and releasing the collar from over the endoscope.

The suturing assembly is adapted for use with an endoscope that does not necessarily have at least two instrument channels. As such, the suturing system can be used with an endoscope independent of the number of instrument channels it contains. Also the suturing system is adapted to not be limited by the size of an endoscope, and can even be used with the smaller endoscopes that are available in many surgical settings and which can be more easily advanced through a natural orifice.

BRIEF DESCRIPTION OF THE DRAWINGS

FIG. 3 is a broken side elevation view of a suturing device of the endoscopic suturing system of FIG. 1.

FIG. 5 is a cross-section view through line 5-5 in FIG. 3.

FIG. 6 is a perspective view of the distal end of the suturing device of FIG. 3.

FIG. 7 is a view similar to FIG. 6 shown in combination with an endoscope.

DETAILED DESCRIPTION OF THE PREFERRED EMBODIMENTS

With reference to the following description, the terms "proximal" and "distal" are defined in reference to the hand of a user of the device, with the term "proximal" being closer to the user's hand, and the term "distal" being further from the user's hand such as to often be located further within a body of the patient during use.

Figure 1:
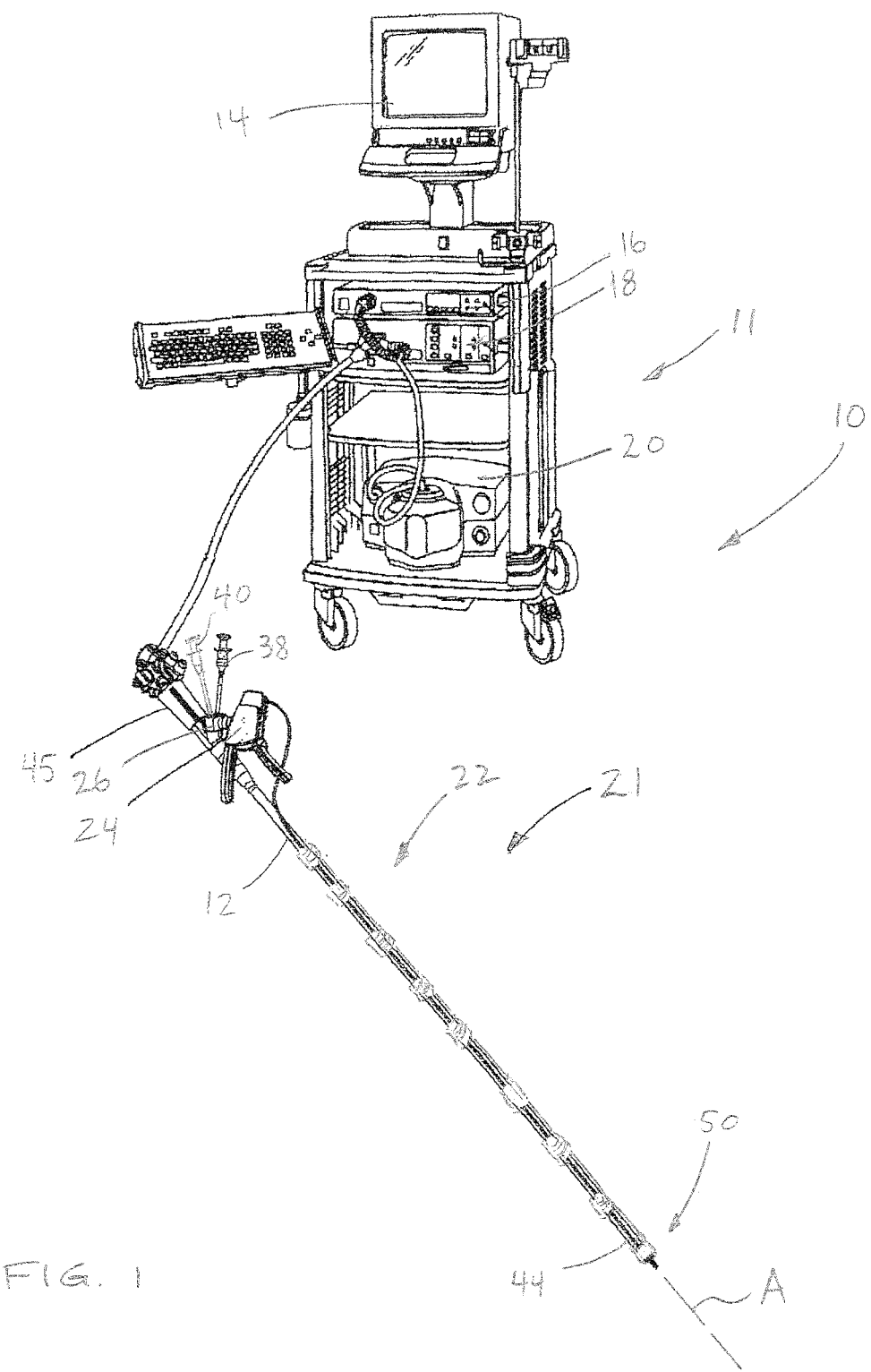
FIG. 1 is a perspective view of an endoscopic suturing system according an embodiment of the invention.
Figure 4:
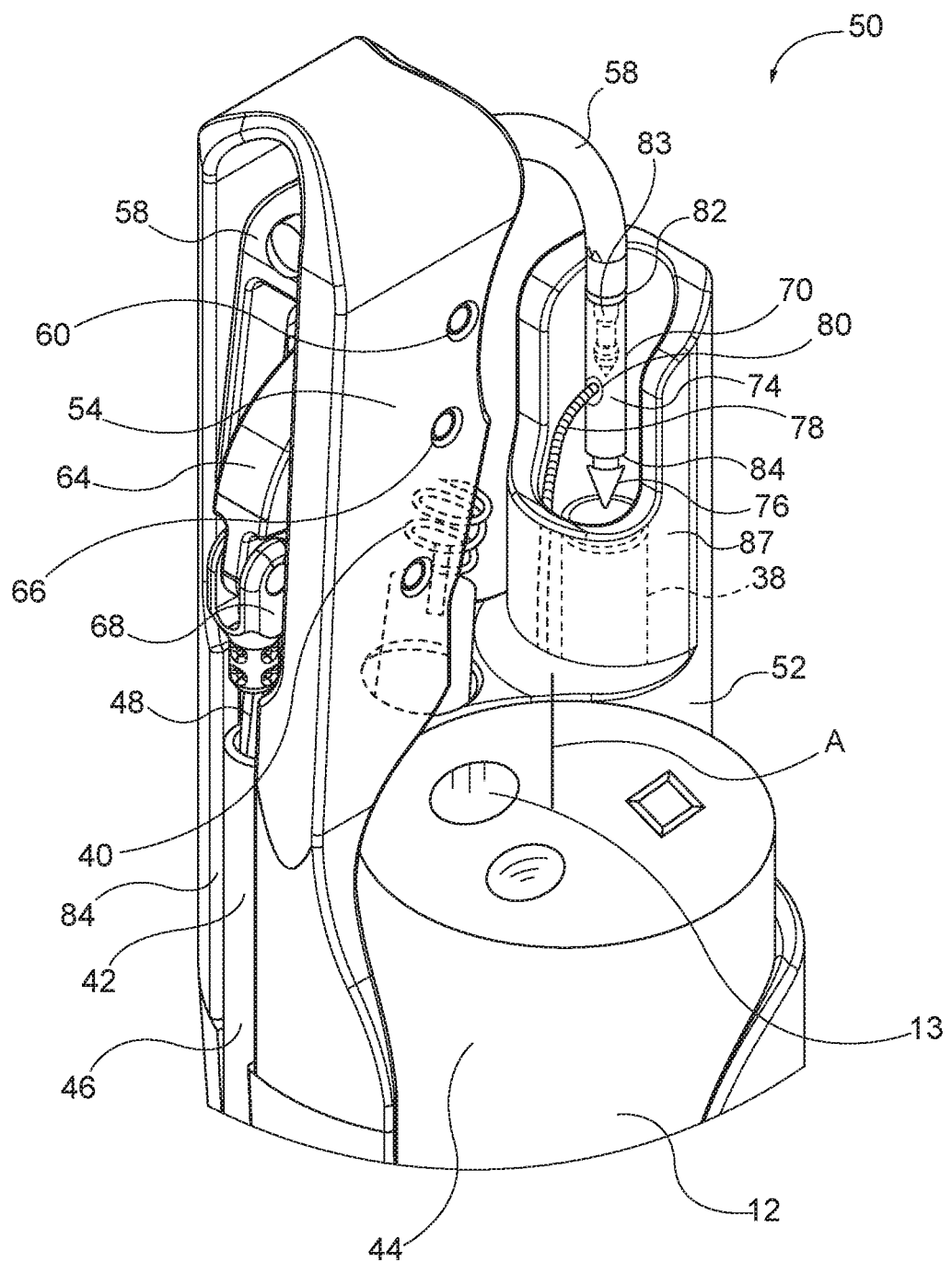
FIG. 4 is a perspective distal end view of an embodiment of a cap assembly attached at the distal end of an endoscope of the endoscope suturing system.

Referring to FIG. 1, an endoscopic treatment system 10 includes an endoscope system 11 and an endoscopic suturing system 22. The endoscope system 11 includes an endoscope 12, a video display unit 14, an image processing device 16, a light source 18, and a suction device 20. In accord with an embodiment, the endoscope 12 has a small profile, generally 5-10 mm in diameter. However, the size of the endoscope is not critical, and elements described herein can be adapted for endoscopes of other sizes. In the embodiment shown, the endoscope 12 has a single instrument channel 13 (FIG. 4). However, the endoscope may have more than one instrument channel or no instrument channel all, as operation of the system does not necessarily require use of the instrument channel through the endoscope. The endoscope 12 includes a distal end 44 and a proximal end 45 and a longitudinal axis A extending therebetween.

Figure 2:
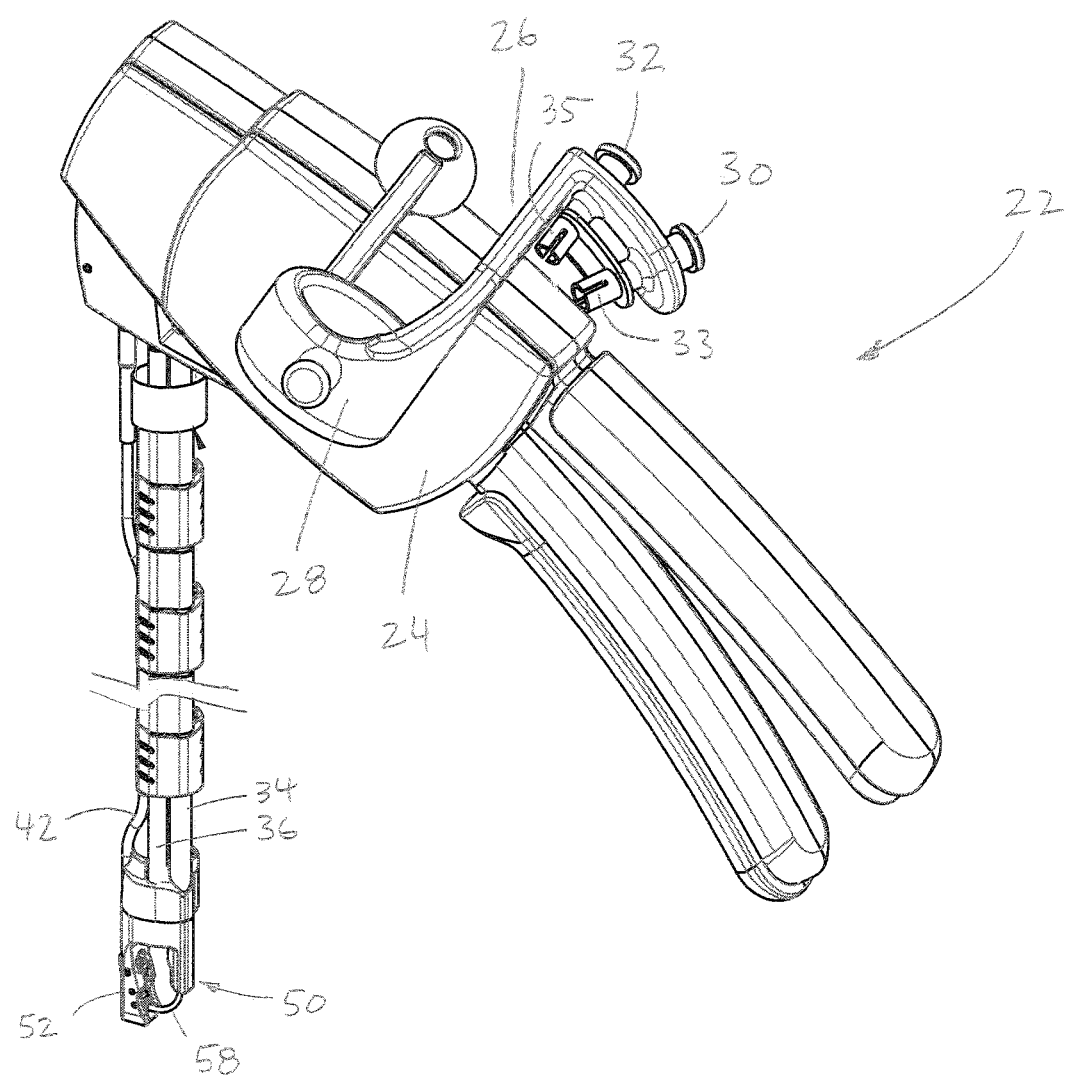
FIG. 2 is a proximal perspective view of a suturing device of the endoscopic suturing system of FIG. 1.

The suturing system 21 includes a suturing device 22 (FIG. 2), a needle assembly 70 (FIG. 4) movable through tissue by the suturing device 22, and first and second devices 38, 40 used in association with the suturing device 22 (FIGS. 2 and 4).

Referring to FIGS. 2 and 3, the suturing device 22 has a proximal operable handle 24 provided with a mounting bracket 26 and a collar 28 at which the handle is removably coupled to endoscope 12. The bracket 26 includes first and second instrument ports 30, 32 at which instruments can be received into first and second lumen 34, 36, respectively. First and second tubular connectors 33, 35 are aligned with the ports 30, 32 that couple the ports 30, 32 to the first and second lumen 34, 36.

A transmission assembly 42 includes a transmission sheath 46 and a transmission cable 48 displaceable within the transmission sheath 46 are coupled to the handle 24. The transmission sheath 46 is coupled relative to a first portion of the handle (i.e., a stationary member), and the transmission cable 48 is coupled to a second portion of the handle (i.e., a movable lever), such that when the handle 24 is operated the cable 48 is displaced within the transmission sheath 46.

The first and second lumens 34, 36 and the transmission assembly 42 extend from the proximal handle 24, along the outside of the endoscope 12, to a distal cap assembly 50. The distal cap assembly 50 is adapted to be mounted at the distal end 44 of the endoscope 12, and the handle 24 remotely operates the cap assembly 50 via the transmission assembly 42.

Referring to FIG. 4, the cap assembly 50 includes a mount 54, U-shaped support bracket 54 extending distally from the mount, and a needle arm 58 rotatably mounted on the bracket 52 with a first pin 60. A bell crank 64 is rotatably mounted at a second pin 66 on the support bracket 54 and engages the needle arm 58 at intermeshing gears (not shown). The distal end of the transmission cable 48 of the transmission assembly 42 is attached to the bell crank 64 at a clevis 68. When the transmission assembly 42 is operated by the handle 24, it results in rotation of the bell crank 64 and consequent rotation of the needle arm 58 between the open and closed positions.

The needle assembly 70 is coupled to a needle mount 83 at an end of the needle arm 58. The needle assembly 70 includes a tubular needle body 74, a needle tip 76, and suture 78 coupled to the needle body. The needle body 74 includes a side opening 80 through which the suture 78 extends, a first end 82 at which the needle assembly is coupled to the needle mount 83, and a second end 84 to which the tip 76 is coupled. The tip 76 defines a tissue-piercing taper. The suture 78 may be formed of any materials commonly available for surgical suture such as nylon, polyolefins, PLA, PGA, stainless steel, nitinol and others. One suitable needle assembly is described in more detail in previously incorporated U.S. Pat. No. 9,198,562.

Turning to FIG. 5, the mount 52 of the cap assembly 50 also includes a side recess 85 into which the transmission assembly 42 is received, and a first throughbore 86 and a second throughbore 88. The first throughbore 86 is positioned in alignment with both the needle mount 83 of the needle arm 58 and needle assembly 70 when the needle arm 58 is in the closed position. A tissue guide 87 extends distally on the mount 52 from over the first throughbore 86 and provides a surface on which to stabilize tissue as it is pierced by the needle assembly 70. The second throughbore 88 is positioned between the first throughbore 86 and the support bracket 54. More particularly, the axial center of the second throughbore 88 is positioned between the first throughbore 86 and the pin 60 (or axis) on which the end effector rotates. The first and second throughbores 86, 88 may be parallel to each other and the longitudinal axis A of the endoscope, or the second throughbore 88 may be obliquely angled relative to the first throughbore 86 so as to direct the second device 40 at a particular orientation into the needle path, as described further below. The mount 52 is structured such that when the cap assembly 50 is coupled to the endoscope 12, as described below, the first and second throughbores 86, 88 are positioned radially outside the profile of the endoscope.

Referring to FIGS. 3 and 5, the distal end of the first lumen 34 is fixed in the first throughbore 86, and its proximal end is coupled to a first connector 33 on the handle bracket 26. The distal end of the second lumen 36 is fixed in the second throughbore 88, and its proximal end is coupled the second connector 35 on the handle bracket 26. The first and second lumen 34, 36 may be defined by discrete catheters (as shown in FIGS. 3 and 6) or may be defined as separate lumen of a common catheter. Further, the catheters 34, 36 (or common catheter) may be covered in a common sheath 89 along at least a portion of their lengths. The common sheath 89 may extend along the entire length of the catheters 34, 36, a partial length, or may be provided in sections along selected portions of the catheters 34, 36.

Turning to FIGS. 1, 3, 4 and 6, the first lumen 34 is adapted to receive a first device 38 that has a distal end effector that can receive and grasp the needle assembly 70. The second lumen 36 is adapted to receive a second device 40 that has a distal end effector that can engage tissue, and draw the tissue back into the path of the needle so that the tissue can be pierced by the needle assembly 70 as the needle assembly is moved from the open to the closed position.

The cap assembly 50 is secured to the distal end 44 of the endoscope 12 with a peripheral engagement structure that is adapted to be positioned about greater than 180° of the circumference of the distal end of the endoscope. In one embodiment, the structure is a cap clip 90 provided in abutting relationship to the mount, and preferably integrated with the mount 52. The clip 90 includes an opening 92, and an arm 94 that may be resiliently deformed to allow the distal end 44 of the endoscope 12 access through the opening 92 and then released to capture the distal end of the endoscope within the clip. The clip 90 may be formed from ABS plastic, other suitable plastics, elastic materials, as well as polymer-coated metals. The distal end of the clip 90 abuts against the proximal end of the mount 52. The first and second lumen 34, 36 extend within the clip 90, and a peripheral recess 96 is provided in the clip to receive the transmission assembly in a relatively flush configuration. A tape or cohesive banding 98 may be used over the clip 90 and distal end 44 of the endoscope to additionally secure the cap assembly relative to the endoscope during use. By way of example, a surgical-grade tape or silicone cohesive banding may be used.

Referring to FIGS. 3 and 6, a plurality of ancillary clips 100 are provided about the first and second lumen 34, 36 and transmission assembly 42 and forming a body that is adapted to extend greater than 180° about the circumference of the endoscope 12. The clips are adapted to secure the first and second lumen 34, 36 and transmission assembly 42 at various displaced locations to the endoscope 12. The ancillary clips 100 include transverse slots 102 that may be filled with a material or an adhesive 104, such as a polymer and optionally silicone. The filling material 104 has a higher coefficient of friction than the body of the clip to enhance the grip of the clip about the endoscope. The ancillary clips 100 are longitudinally spaced apart along the lumens 34, 36 and transmission assembly 42 to allow suitable flexure and operation of the first and second devices 38, 40 extending within the first and second lumen 34, 36, as well as flexure and operation of the transmission assembly 42. The spaced apart ancillary clips 100 may be interposed with portions of the common sheath 89.

In light of the above, the suturing device may be prepared for use in conjunction with an endoscope as follows. The cap assembly 50 is attached to the distal end 44 of the endoscope 12, with the cap clip 90 being opened to laterally receive the endoscope, and then released to secure the cap assembly 50 and endoscope 12 relative to each other. The first and second lumen 34, 36 and transmission assembly 42 are coupled along the endoscope 12 with the ancillary clips 100. The collar 28 is properly positioned at the proximal handle 45 of the endoscope 12. The first device, a needle capture instrument 38 loaded with a needle assembly 70, is advanced through the first port 32, into the first lumen 34 and to the cap assembly 50. Suitable needle capture devices 38 are described in detail in previously incorporated U.S. Pat. No. 8,679,136. The needle assembly 70 is loaded onto the needle arm 58, with the suture 78 extending parallel to the needle capture instrument 38 within the first lumen 34.

Figure 8:
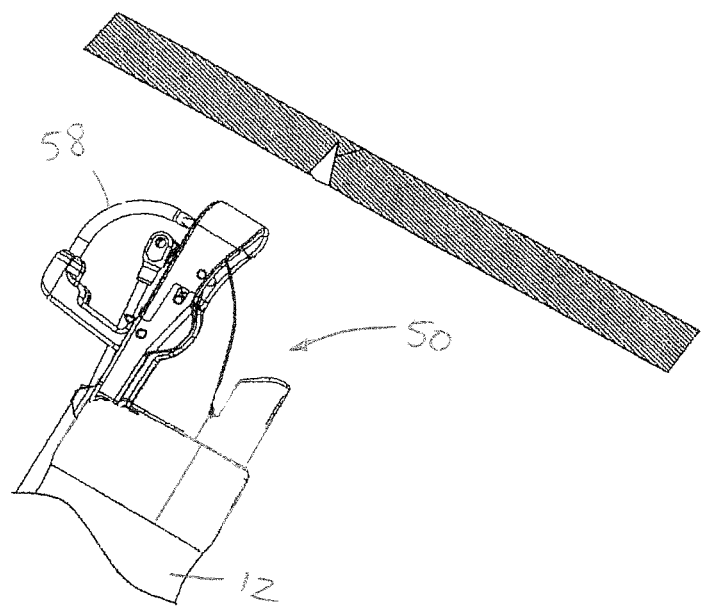
FIGS. 8-12 illustrate use of the endoscopic suturing system to endoscopically suture tissue.
Figure 9:
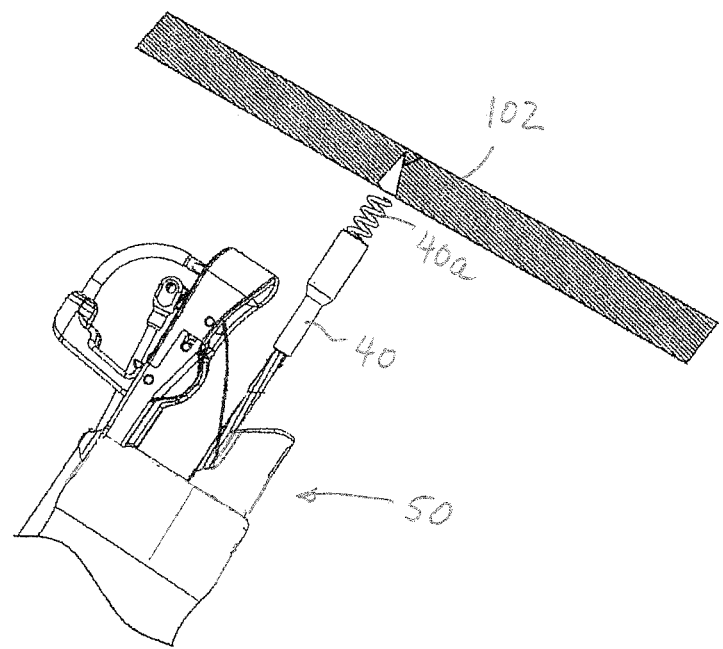
Figure 10:
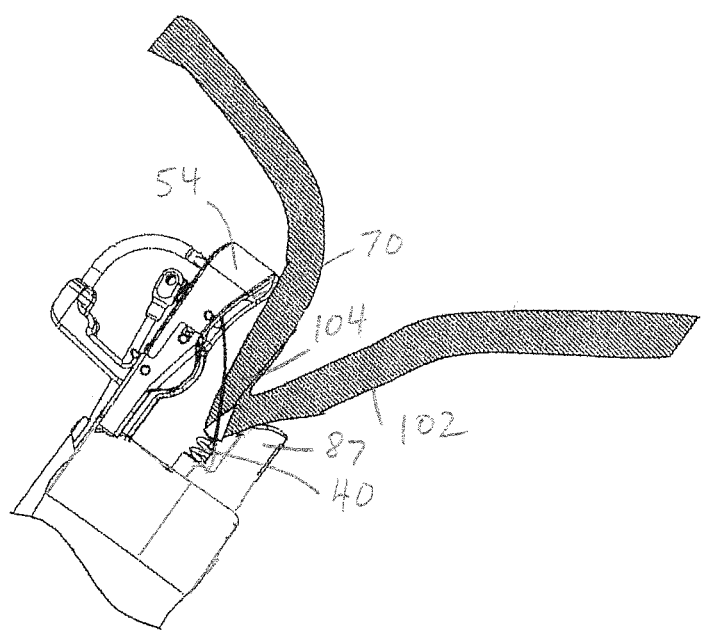
Figure 11:
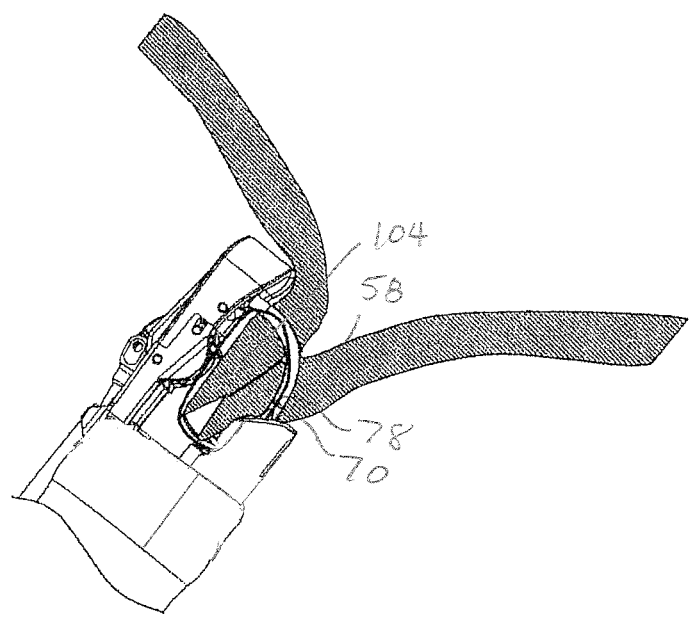
Figure 12:
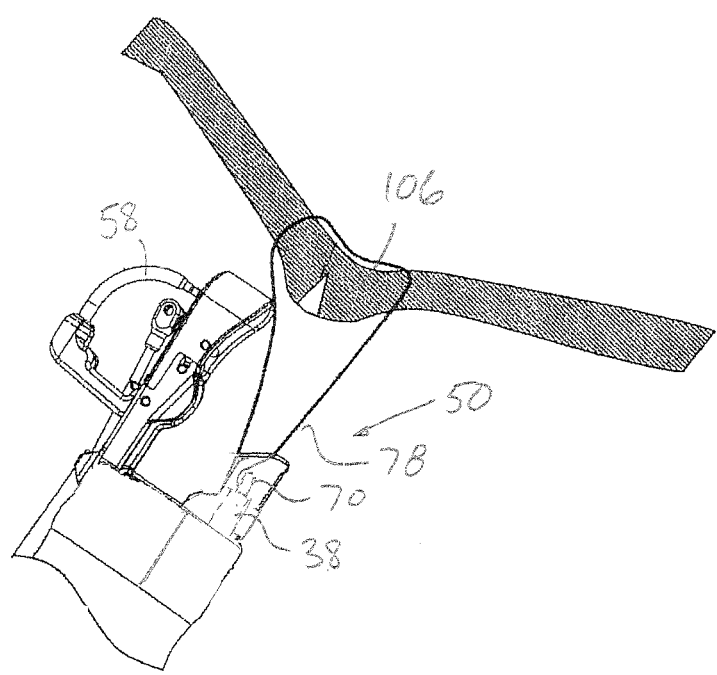

With reference to FIGS. 1 and 8, the distal end of the endoscope 12 and cap assembly 50 of the suturing device 22 are advanced into a natural orifice of a patient, optionally through a guide tube (not shown), and approached to target tissue 102. The handle 24 of the suturing device 22 is operated to move the needle arm 58 into the open position, as shown in FIG. 8. Turning to FIG. 9, the end effector of the second device, e.g., a tissue retractor 40 having a helical coil 40a at its distal end, is advanced through the second port 32, into the second lumen 36 (FIG. 3) and out the second throughbore 88 (FIG. 5), and beyond the cap assembly 50. Suitable tissue retractor instruments are described in detail in previously incorporated U.S. Ser. No. 13/539,661. Other tissue retractors, including forceps, may also be used. The helical coil 40a is operated to engage target tissue 102. The tissue retractor 40 is withdrawn to draw the tissue 102 against the tissue guard 87 and into a fold 104 located within the path of the needle assembly 70; i.e., between the bracket 54 and needle guide 87, as shown in FIG. 10. The orientation of the second throughbore 88, either parallel or obliquely angled relatively to the first throughbore 86, is adapted to guide the tissue retractor to engage and retract tissue into the needle path. The handle 24 is then operated to move the needle arm 58 into the closed position, thereby piercing the tissue fold 104 and passing the needle assembly 70 with suture 78 through the tissue fold during the movement. When the needle arm 58 is in the closed position, the needle is received within the distal end of the needle capture device 38 (FIG. 4). The needle capture device 38 is operated to securely engage the needle 70. The handle 26 is then operated to move the needle arm 58 toward the open position, thereby disengaging the needle arm 58 from the needle assembly 70, which remains in the needle capture device 38 (FIG. 12). The tissue retractor 40 is also released from the tissue and withdrawn back through the second lumen 36. The endoscope 12 is then moved to displace the cap assembly 50 relative to the sutured tissue 106. The needle 70 and suture 78 may be secured onto the tissue, such as by knotting or cinching, or the needle may be repositioned on the needle arm and additional suture loops may be formed within adjacent or other areas of tissue. Once the suturing is complete, the needle arm 58 is returned to a closed position, and the endoscope 12 and suturing device 22 are removed from the patient.

The suturing assembly is then released from over the endoscope by releasing the cap clip and ancillary clips from over the endoscope 12 and releasing the collar 28 from the proximal end of the endoscope.

Figure 13:
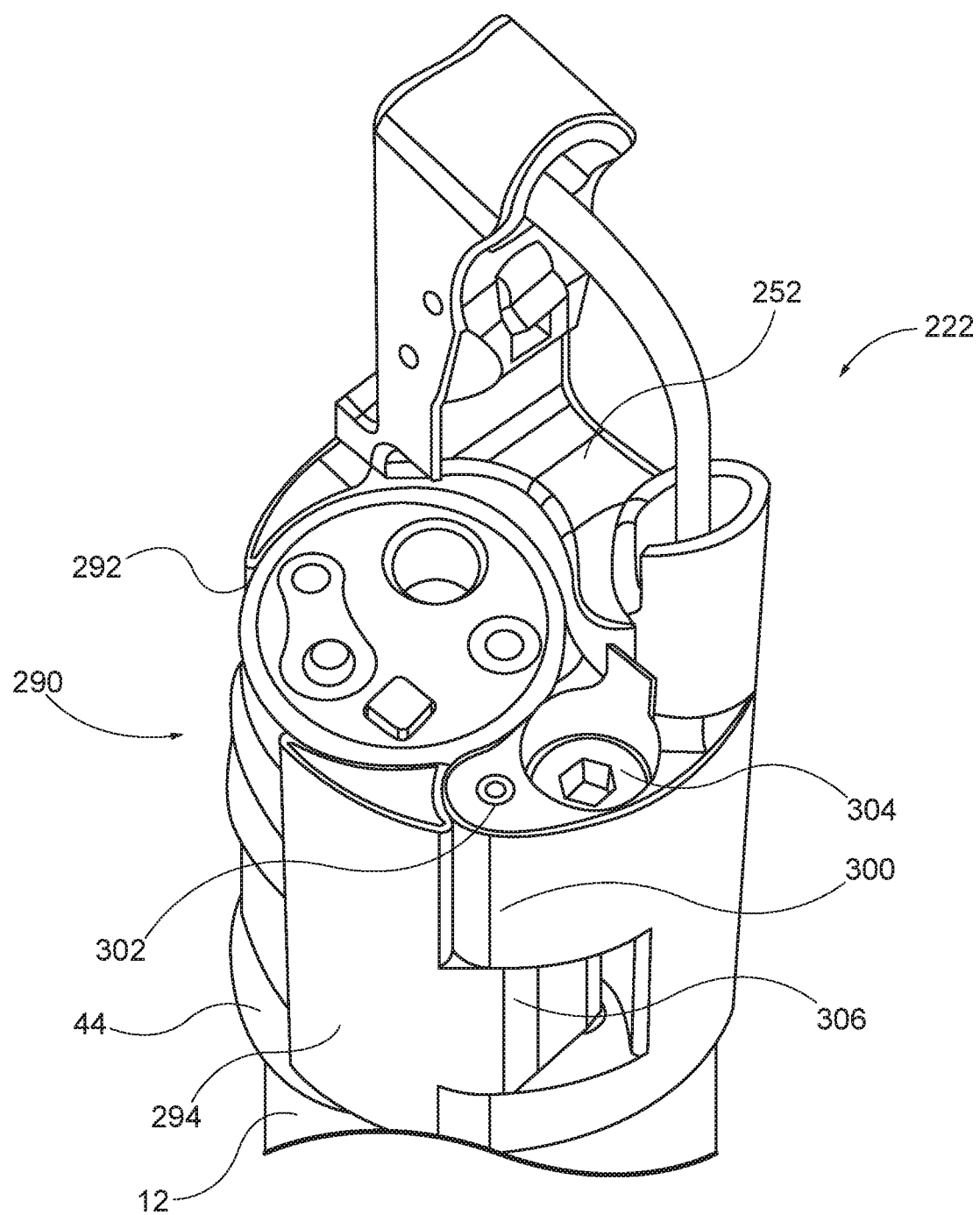
FIG. 13 is a perspective distal end view of another embodiment of a cap assembly attached at the distal end of an endoscope of the endoscope suturing system.

Turning now to FIG. 13, another embodiment of a suturing system 222 is shown that is substantially similar to suturing system 22 described above but which includes variations on the peripheral engagement structure. In distinction from the cap clip 90 with resilient arm 94 of the earlier embodiment, the suturing system 222 includes an engagement structure 290 defined by a recess 292 (indicated at the location of the distal end 44 of the endoscope 12) and an independently rotatable arm 294 that is structured to retain the endoscope within the recess when in a closed position. The arm 294 is mounted at a hinge 300 on a hinge pin 302, and can be rotated open to allow insertion of the distal end 44 of the endoscope 12 into the recess, and then rotated closed to secure the endoscope by the arm 294. The arm 294 may be associated with a lock that when released allows relatively free rotation of the arm 294 on its hinge 300 and when locked fixes the position of the arm 294. The lock may be defined by a set screw 304 that is rotated into and out of engagement with a portion 306 of the hinge 300. Alternatively, the set screw 304 may operate as a cam on the hinge or other portion of the arm to rotate the arm 294 into a closed position as the set screw 304 is rotated in a one direction, and a release on the cam as the set screw is rotated in the opposite direction. Other cam structures can also be used. As yet another alternative, the arm 294 may be biased with a spring located, by way of example, at the hinge 300 and which automatically forces the arm 294 toward a closed position to secure the endoscope once the endoscope is positioned within the recess 294. The arm 294 may be integrated with the mount 252, or may be provided in an abutting relationship.

The suturing assemblies described above are adapted for use with an endoscope that does not necessarily have at least two instrument channels. As such, the suturing system can be used smaller endoscopes that are available in many surgical setting and which can be more easily advanced through a natural orifice.

There have been described and illustrated herein embodiments of a suturing system as well as a surgical treatment system, as well as methods of using the same. While particular embodiments of the invention have been described, it is not intended that the invention be limited thereto, as it is intended that the invention be as broad in scope as the art will allow and that the specification be read likewise. Thus, while particular instruments and devices for advancement through the first and second lumen have been disclosed, it will be appreciated that other instruments can also be used through such lumen for like or even different purpose. Also, while the treatment system has been particularly described with respect to a cap assembly having an end effector in the form of a needle arm that carries a needle, it is recognized that alternatively one or more movable end effectors with other structure and purpose can be provided to the cap assembly. Also, while a tissue anchor in the form of a needle assembly has been described, the end effector can deploy different types of tissue anchors, including, e.g., clips. In addition, while a particular needle assembly has been described, other needle assemblies can similarly be used. Also, the size and instrument channel features of the endoscope with which the system is used is not critical, it is appreciated that various prior art systems cannot be properly used in a suturing operation in conjunction with endoscopes having fewer than two instrument channels, one for receiving a needle exchange device and the other for receiving a tissue retractor, whereas the present system is capable of complete operation without the provision of any channels through the endoscope. It will therefore be appreciated by those skilled in the art that yet other modifications could be made to the provided invention without deviating from its scope as claimed.

What is claimed is:

1. An endoscopic treatment system for use with an endoscope having a proximal end and a distal end and a longitudinal axis extending therebetween, the distal end having an end face, the endoscopic treatment system comprising:
   a) a distal cap assembly having an end effector rotatable on a pivot axis between open and closed positions, the end effector having a free end defining an effector axis;
   b) a transmission assembly having proximal and distal ends, the distal end operably coupled to the end effector such that displacement of at least a portion of the transmission assembly rotates the end effector between the open and closed positions;
   c) a proximal handle assembly coupled to the transmission assembly and adapted to effect the displacement of the at least a portion of the transmission assembly to rotate the end effector;
   d) first and second lumens, being discrete from the endoscope and extending from the cap assembly to the proximal handle assembly for receiving instruments therethrough, a distal end of the first lumen in alignment with the free end of the end effector when the end effector is in the closed position, and the second lumen positioned between the first lumen and the pivot axis on which the end effector rotates;
   e) a peripheral engagement structure adapted to be positioned about greater than 180° of a circumference of the distal end of the endoscope, the peripheral engagement structure in an abutting relationship with a proximal end of the cap assembly; and
   f) a plurality of spaced apart ancillary clips, the ancillary clips adapted to retain the transmission assembly and the first and second lumens relative to the endoscope, wherein when the peripheral engagement structure is positioned about the distal end of the endoscope so that the proximal end of the cap assembly abuts the distal end of the endoscope and when the end effector is rotated into the closed position, the effector axis is oriented parallel to the longitudinal axis and lateral of the end face of the endoscope.

2. The endoscopic treatment system according to claim 1, further comprising:
   a needle assembly having a needle and suture, wherein the needle assembly is removably coupled to the end effector.

3. The endoscopic treatment system according to claim 2, wherein:
   when the end effector is in the closed position, the needle assembly is oriented parallel to the longitudinal axis.

4. The endoscopic treatment system according to claim 1, wherein:
   the cap assembly includes a mount supporting the end effector and defining first and second throughbores, and the first and second lumen extend into the first and second throughbores.

5. The endoscopic treatment system according to claim 4, wherein:
   the first and second throughbores are parallel to each other.

6. The endoscopic treatment system according to claim 4, wherein:
   the first and second throughbores are obliquely oriented relative to each other.

7. The endoscopic treatment system according to claim 1, wherein:
   the first and second lumen are defined by discrete catheters.

8. The endoscopic treatment system according to claim 7, further comprising:
   a common sheath covering at least a portion of both discrete catheters.

9. The endoscopic treatment system according to claim 1, wherein:
   the first and second lumen are defined by a common catheter.

10. The endoscopic treatment system according to claim 1, wherein:
    the ancillary clips include slots and said slots include a material having a higher coefficient of friction than that of the clips.

11. The endoscopic treatment system according to claim 1, wherein:
    the peripheral engagement structure comprises a recess and an arm that is resiliently deformed to receive the distal end of the endoscope within the recess.

12. The endoscopic treatment system according to claim 11, wherein:
    the peripheral engagement structure further comprises a tape or banding wrapped around the arm.

13. The endoscopic treatment system according to claim 1, wherein:
    the peripheral engagement structure comprises a recess and an arm that is rotatable on a hinge to receive and then engage the distal end of the endoscope within the recess.

14. The endoscopic treatment system according to claim 13, wherein:
    the arm is rotatable about a hinge pin.

15. The endoscopic treatment system according to claim 13, wherein:
    the peripheral engagement structure further comprises a lock to fix a location of the arm.

16. The endoscopic treatment system according to claim 15, wherein:
    the lock is a set screw.

17. The endoscopic treatment system according to claim 15, wherein:
    the peripheral engagement structure further comprises a cam applies a force against the arm to move and/or retain the arm into a closed position.

18. The endoscopic treatment system according to claim 15, wherein:
    the peripheral engagement structure further comprises a spring that biases the arm into a closed position.

19. The endoscopic treatment system according to claim 1, further comprising:
    the endoscope having the proximal end and the distal end and the longitudinal axis extending therebetween, wherein the endoscopic treatment system is coupled to the endoscope.

20. The endoscope treatment system according to claim 19, wherein:
    the endoscope has at most one instrument channel for receiving instruments therethrough.

21. The endoscopic treatment system according to claim 1, wherein:
    the distal end of the first lumen is fixed relative to the pivot axis.

22. An endoscopic treatment system for use with an endoscope having a proximal end and a distal end with an end face, a longitudinal axis extending therebetween, and a circumference, comprising:
   a) a distal cap assembly having an end effector rotatable on a pivot axis between open and closed positions, the end effector having a free end defining an effector axis;
   b) a transmission assembly having proximal and distal ends, the distal end operably coupled to the end effector such that displacement of at least a portion of the transmission assembly rotates the end effector between the open and closed positions;
   c) a proximal handle assembly coupled to the transmission assembly and adapted to effect the displacement of at the least a portion of the transmission assembly to rotate the end effector;
   d) first and second lumens being discrete from the endoscope and extending from the cap assembly to the proximal handle assembly for receiving instruments therethrough, a distal end of the first lumen in alignment with the free end of the end effector when the end effector is in the closed position, and the second lumen positioned between the first lumen and the pivot axis on which the end effector rotates; and
   f) a plurality of clips spaced apart along the transmission assembly and first and second lumen, the clips each having a body adapted to extend greater than 180° about the circumference of the endoscope, the clips defining slots filled with a material having a higher coefficient of friction than the body,
      wherein when the clips are positioned about the distal end of the endoscope so that the proximal end of the distal cap assembly abuts the distal end of the endoscope and when the end effector is rotated into the closed position, the effector axis is oriented parallel to the longitudinal axis and lateral of the end face of the endoscope.

23. The endoscopic treatment system according to claim 22, wherein:
   the distal end of the first lumen is fixed relative to the pivot axis.

24. An endoscopic treatment system for use with an endoscope having a proximal end and a distal end and a longitudinal axis extending therebetween, the distal end having an end face, the endoscopic treatment system comprising:
   a) a distal cap assembly having an end effector rotatable on a pivot axis between open and closed positions, the end effector having a free end defining an effector axis;
   b) a transmission assembly having proximal and distal ends, the distal end operably coupled to the end effector such that displacement of at least a portion of the transmission assembly rotates the end effector between the open and closed positions;
   c) a proximal handle assembly coupled to the transmission assembly and adapted to effect the displacement of at the least a portion of the transmission assembly to rotate the end effector;
   d) first and second lumens being discrete from the endoscope and extending from the cap assembly to the proximal handle assembly for receiving instruments therethrough, a distal end of the first lumen in alignment with the free end of the end effector when the end effector is in the closed position, and the second lumen positioned between the first lumen and the pivot axis on which the end effector rotates; and
   e) a peripheral engagement structure adapted to be positioned about greater than 180° of a circumference of the distal end of the endoscope, the peripheral engagement structure integrated with the cap assembly,
      wherein when the peripheral engagement structure is positioned about the distal end of the endoscope so that the cap assembly abuts the distal end of the endoscope and when the end effector is rotated into the closed position, the effector axis is oriented parallel to the longitudinal axis and lateral of the end face of the endoscope.

25. The endoscopic treatment system according to claim 24, wherein:
   the peripheral engagement structure includes a resilient arm.

26. The endoscopic treatment system according to claim 24, wherein:
   the peripheral engagement structure includes an arm rotatable on a hinge.

27. The endoscopic treatment system according to claim 24, wherein:
   the distal end of the first lumen is fixed relative to the pivot axis.

* * * * *